United States Patent [19]

Braida-Valerio et al.

[11] Patent Number: 6,076,530
[45] Date of Patent: Jun. 20, 2000

[54] PROCESS FOR THE TREATMENT OF HUMAN HAIR WITH THE AID OF FATTY-CHAIN AMIDES AND STEAM

[75] Inventors: Damarys Braida-Valerio, Paris; Jean-Michel Sturla, St Cloud, both of France

[73] Assignee: L'Oreal, Paris, France

[21] Appl. No.: 08/792,231

[22] Filed: Jan. 31, 1997

Related U.S. Application Data

[63] Continuation of application No. 08/509,816, Aug. 1, 1995, abandoned.

[30] Foreign Application Priority Data

Aug. 2, 1994 [FR] France .................................. 94-09583

[51] Int. Cl.$^7$ ...................................................... A61K 7/06
[52] U.S. Cl. ........................... 132/206; 424/47; 424/70.1; 424/70.11; 424/DIG. 1; 424/70.17; 132/202; 132/203
[58] Field of Search ............................. 424/45, 47, 70.1, 424/DIG. 1, 70.11, 70.17; 132/202, 203, 206

[56] References Cited

U.S. PATENT DOCUMENTS 3,702,616   11/1972   Mercer .
4,166,473   9/1979   Bauer et al. .

FOREIGN PATENT DOCUMENTS

| 0 227 994 | 7/1987 | European Pat. Off. . |
| 2 273 492 | 1/1976 | France . |
| 2 673 179 | 8/1992 | France . |
| 92/057647 | 4/1992 | WIPO . |
| 93/02656 | 2/1993 | WIPO . |
| 94/07844 | 4/1994 | WIPO . |

OTHER PUBLICATIONS

Zviak, C. (1986). The Science of Hair Care. Marcel Dekker, Inc., New York & Basel, pp. 149–155, 184–189.

*Primary Examiner*—Raj Bawa
*Attorney, Agent, or Firm*—Finnegan, Henderson, Farabow, Garrett & Dunner, L.L.P.

[57] ABSTRACT

An improved process for the treatment of human keratinous fibers, in particular hair, with a view especially to decreasing and/or preventing damage to the latter by bringing, for a period not exceeding 2 minutes, a gas containing steam and whose temperature is at least 75° C., into contact with human keratinous fibers to which there has been applied a composition containing at least one amide compound which has at least one fatty chain with the exception of coprah diethanolamide and subsequently cooling the fibers thus treated. This process improves the binding of the amide on and/or in the hair, and results in an improvement in the cosmetic properties, in particular softness and smoothness.

17 Claims, No Drawings

PROCESS FOR THE TREATMENT OF HUMAN HAIR WITH THE AID OF FATTY-CHAIN AMIDES AND STEAM

This application is a continuation of application Ser. No. 08/509.816, filed Aug. 1. 1995, now abandoned.

The present invention relates to an improved process for the treatment of human keratinous fibers, in particular hair, with a view especially to decreasing, preventing or both decreasing and preventing the damage to the fibers. This process is useful especially in the province of hairdressing, beauty, and cosmetics and particularly in professional parlours. More precisely, it relates to a process using steam and particular treating substances based on an amide compound having at least one fatty chain, with the exception of coprah diethanolamide.

It is well known that hair can be generally sensitized (i.e., damaged) to various degrees by the action of atmospheric agents, mechanical or chemical hair treatments such as dyeing, bleaching and permanent waving, or combinations of atmospheric agents, mechanical and chemical hair treatments. Hair which is thus sensitized often becomes difficult to untangle and to style.

Thus, with the aim of treating and/or protecting the hair fiber, it has already been proposed to employ amides which have a fatty chain. However, the behaviour of these products on the hair still appears to be inadequate. In particular, it is found that a single shampooing removes a large proportion of the amides which have deposited on the hair.

The protection and care provided by the amides is proportional to the quantities thereof which are present on the hair. Consequently, the inventors have sought to improve the binding of the amides to hair.

Thus, following considerable research, the inventors have unexpectedly and surprisingly found that these objectives, and others, could be obtained by using, according to certain special conditions, steam on human keratinous fibers treated beforehand with amides which have at least one fatty chain with the exception of coprah diethanolamide. This discovery underlies the present invention.

The process according to the invention makes it possible to increase the quantity of amide bound on the hair. In fact, the quantity of amides remaining on the hair after a rinsing or a shampooing is greater in the context of the process according to the invention than when no hot steam is employed, as will be demonstrated below in the examples.

This process also makes it possible to improve the cosmetic properties, in particular the softness and the smoothness of the hair.

Thus, a new process for the treatment of human keratinous fibers, and in particular of hair, is proposed according to the present invention, the said process having the following steps:

(i) applying to human keratinous fibers a composition containing at least one amide compound which has at least one fatty chain with the exception of coprah diethanolamide;

(ii) placing in contact with these treated human keratinous fibers a gas which contains steam and which is at a temperature of at least 75° C.; and (iii) cooling said fibers thus treated.

Although the description which follows is worded essentially in relation to the particular case of hair treatment, it will be noted here that the process according to the invention is applicable to any human keratinous material in general, and especially eyelashes, moustaches, and body hair.

The treating hot gas preferably contains at least 1% by volume of steam. In addition to steam, the carrier (or support) gas may contain solvent vapour, as well as gases such as oxygen or nitrogen, gas mixtures such as air, or indeed other vaporizable compounds.

By way of solvents which may be advantageously employed for the production of vapour (water-solvent mixtures), use is made more particularly of cosmetically acceptable organic solvents like, for example, alcohols, such as ethanol, isopropanol, benzyl alcohol, and phenylethyl alcohol, glycols or glycol ethers, such as, for example, ethylene glycol and its monomethyl, monoethyl and monobutyl ethers, propylene glycol, butylene glycol, dipropylene glycol and alkyl ethers like diethylene glycol monobutyl ether.

According to the present invention, the gas preferably consists either solely or essentially of steam or a mixture of water and air.

The temperature of the gas is preferably at least 85° C. and is more particularly from 85° C. to 150° C.

According to an important characteristic of the process according to the invention, the contact time between the treating hot gas and the fiber must be brief and preferably should not exceed 2 minutes. The gas is preferably brought into contact with the fiber for a period ranging from 0.01 second to 30 seconds, and more preferably from 1 second to 10 seconds. The application of the gas may, of course, be repeated a number of times on the same fiber, each operation being performed according to a duration as indicated above.

A preferred embodiment of the process according to the invention consists in first applying to the hair a composition containing fatty-chain amides and in then subjecting these locks of hair, thus impregnated with fatty-chain amides, to the brief action of steam according to the above-mentioned conditions. Subsequently, the locks of hair thus treated with steam, are cooled, preferably rapidly, for example by directing onto or through them a stream of air at ambient temperature or by drawing a stream of ambient air through the locks of hair. The hair may also be cooled by allowing it to stand at room temperature after the steam treatment.

The production of a hot gas including steam may take place with the aid of any apparatus which is known per se and designed for this purpose. However, according to the present invention, use is preferably made of an apparatus such as that described in French Patent Application FR-A-2 273 492, the disclosure of which is hereby incorporated by reference, or any other equivalent apparatus, which is actually particularly suitable in the present case (pointform, uniform and homogeneous treatment of the fibers, without risk of overheating, with integral cooling aftertreatment).

The amide compounds which can be employed according to the invention have at least one fatty chain preferably containing from 8 to 40 carbon atoms. It is possible, for example, to employ the erucamide offered under the trade name Crodamide ER by the Croda Company or the behenamide $R_3$ denotes a hydrogen atom or a saturated or unsaturated $C_{16}$–$C_{27}$ hydrocarbon radical, it being possible for this radical to be substituted by one or more $C_1$–$C_{14}$ alkyl radicals; $R_3$ may also denote a $C_{15}$–$C_{26}$ α-hydroxyalkyl radical, the hydroxyl group being optionally esterified by a $C_{16}$–$C_{30}$ α-hydroxy acid, $R_4$ denotes a hydrogen atom, a saturated or unsaturated $C_{16}$–$C_{27}$, hydrocarbon radical or a radical —$CH_2$—CHOH—$CH_2$—O—$R_6$ in which $R_6$ denotes a $C_{10}$–$C_{26}$ hydrocarbon radical, $R_5$ denotes a hydrogen atom or a mono- or polyhydroxylated $C_1$–$C_4$ hydrocarbon radical.

Among the compounds of formula (I), preference is given to the ceramides and/or glycoceramides described by Downing in Arch. Dermatol., vol. 123, 1381–1384, 1987, the disclosure of which is hereby incorporated by reference, or those described in French Patent Application FR-2 673 179, the disclosure of which is hereby incorporated by reference.

The ceramides more particularly preferred according to the invention are the compounds of formula (I) in which $R_1$ denotes a saturated or unsaturated alkyl derived from $C_{16}$–$C_{22}$ fatty acids, $R_2$ denotes a hydrogen atom, and $R_3$ denotes a $C_{15}$ saturated linear radical.

Such compounds are, for example:
N-linoleoyldihydrosphingosine,
offered under the trade name Kemamide B by the Witco Company.

The preferred amide compounds according to the invention may correspond to the general formula (I):

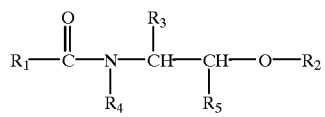

in which:
$R_1$ denotes either
a $C_9$–$C_{30}$, saturated or unsaturated, linear or branched hydrocarbon radical, it being possible for this radical to be substituted by one or more hydroxyl groups optionally esterified by a $C_{16}$–$C_{30}$ saturated or unsaturated fatty acid,
or
a radical R"—(NR—CO)$_n$—R' in which n is equal to 0 or 1, R denotes hydrogen or hydroxyethyl, and R' and R" are hydrocarbon radicals in which the sum of the carbon atoms is from 9 to 30, R' being a divalent radical,
$R_2$ denotes a hydrogen atom or a (glycosyl)$_n$, (galactosyl)$_m$ or sulphogalactosyl radical, wherein n is an integer varying from 1 to 4 and m is an integer varying from 1 to 8,
N-oleoyidihydrosphingosine,
N-palmitoyldihydrosphingosine,
N-stearoyldihydrosphingosine,
N-behenoyldihydrosphingosine,
or the mixtures of these compounds.

It is also possible to employ the compounds of formula (I) in which $R_1$ denotes a saturated or unsaturated alkyl radical derived from fatty acids, $R_2$ denotes a galactosyl or sulphogalactosyl radical, and $R_3$ denotes a —CH=CH—(CH$_2$)$_{12}$—CH$_3$ group.

For example, it is possible to employ the product consisting of a mixture of glycoceramides, sold under the trade name Glycocer by the Company Waitaki International Biosciences.

It is also possible to employ the compounds of formula (I) which are described in Patent Applications EP-A-0227994 and WO94/07844, the disclosures of which are hereby incorporated by reference. Such compounds are, for example, Questamide H (bis(N-hydroxyethyl-N-cetyl) malonamide) sold by the Company Quest, and N-(2-hydroxyethyl)-N-(3-cetyloxy-2-hydroxypropyl)cetylamide.

It is also possible to employ the N-docosanoyl-N-methyl-D-glucamine described in Patent Application WO92/05764, the disclosure of which is hereby incorporated by reference.

The amide concentration may vary approximately from 0.0001% to 30% by weight relative to the total weight of the composition, and preferably approximately from 0.001 to 10%.

The compositions may be in any form usually employed in the field of hair compositions for topical use, such as, for example, more or less thickened or gelled liquid, cream, mousse, lotion, gel, paste, emulsion, aerosol or any other appropriate form.

The amide-based compositions may thus, and generally, contain all the various conventional additives which are employed in the field of the preparation of hair compositions for topical use and may be chosen, for example, from UV filters, thickening agents, penetrating agents, antioxidants, sequestering agents, opacifying agents, buffers, surface-active agents chosen from nonionic surfactants, such as alkyl polyglycosides, cationic surfactants, anionic surfactants and amphoteric surfactants, solubilizing agents, emollients, colorants, perfumes and preserving agents.

The amide-based compositions employed in the scope of the present invention, which are preferably intended to be applied to hair, preferably exhibit a pH of from 3 to 11. If necessary, this pH may be adjusted to the desired value by the addition, depending on the case, either of basifying agents or of acidifying agents, which are usual and known as being cosmetically acceptable.

Concrete examples illustrating the invention will now be given, without any limitation whatever being implied. For the purposes of a significant comparison, the same starting locks of hair (before treatment) have been employed for all the examples.

EXAMPLE 1

An amide-based composition 1 exhibiting the following characteristics was employed:

| | |
|---|---|
| N-oleoyldihydrosphingosine | 0.5 g |
| Quaternium-27 (Rewoquat W75 PG) | 2 g |
| Water q.s. | 100 g |

This composition was packaged in a pump bottle releasing 150-$\mu$l doses by spraying.

The procedure was the following: 3 sprays of the above composition were applied onto a lock of bleached hair; the lock was then treated for 3 seconds by means of a jet of gas containing essentially only steam and the temperature of which was 85° C.; thus treated, the lock was then rapidly cooled by means of a stream of ambient air and finally the lock was washed with a standard shampoo (0.5 g per lock for 30 seconds) and then rinsed 3 times, each time with 2 runs in 200 ml of water being performed. The lock was then dried at ambient temperature.

To compare the quantity of amide bound on the hair, the same quantity of above composition 1 was applied to a lock of hair of the same quality, which was not treated with steam. The procedure was otherwise identical.

Each lock was divided into two and ceramide was extracted by extraction with dichloromethane (2 times 20 ml for one hour at ambient temperature with mechanical stirring). The amides were then separated from the hair lipids by TLC (thin layer chromatography). The amide was then determined by photodensitometry after carbonization with a solution containing 3% by weight of sulphuric acid, followed by heating in the oven at 180° C. (a known quantity of amide is employed as reference).

The results were collected in the following table:

| | Quantity of ceramide extracted per g of hair |
|---|---|
| Treatment with steam | 36 μg ± 1.4 |
| Treatment without steam | 16 μg ± 1.4 |

As is evident, the quantity of ceramide which was bound on the hair was much greater when the hair is treated with steam at 85° C.

EXAMPLE 2

The following lotion was prepared:

| | |
|---|---|
| Hydroxycetamide (Questamide H from Quest Int.) | 0.1 g |
| Ethanol q.s. | 100 g |

If the composition is applied to hair in the same way as in Example 1, it is predicted that similar results will be obtained.

EXAMPLE 3

The following composition was prepared:

| | |
|---|---|
| N-(2-hydroxyethyl)-N-(3-cetyloxy-2-hydroxypropyl)cetylamide | 0.1 g |
| Quaternium-27 (Rewoquat W75 PG) | 0.5 g |
| Water q.s. | 100 g |

If the composition is applied to hair in the same way as in Example 1, it is predicted that similar results will be obtained.

What is claimed is:

1. A process for the treatment of human keratinous fibers comprising the steps of:
    (i) applying to human keratinous fibers a composition containing at least one amide compound which has at least one fatty chain with the exception of coprah diethanolamide;
    (ii) placing in contact with said human keratinous fibers a gas which contains steam and which is at a temperature of at least 75° C.;
    (iii) cooling said fibers after said steam treatment; and wherein said human keratinous fibers are hair.

2. The process of claim 1, wherein said gas has a temperature of at least 85° C.

3. The process of claim 2, wherein said temperature is from 85° C. to 150° C.

4. The process of claim 1, wherein a human keratinous fiber is placed in contact with said gas for a period not exceeding 2 minutes.

5. The process of claim 4, wherein said gas is placed in contact with said fiber for a period ranging from 0.01 second to 2 minutes.

6. The process of claim 5, wherein said gas is placed in contact with said fiber for a period ranging from 0.01 second to 30 seconds.

7. The process of claim 6, wherein said gas is placed in contact with said fiber for a period ranging from 1 second to 10 seconds.

8. The process of claim 1, wherein the application of said gas is repeated a number of times on the same fiber.

9. The process of claim 1, wherein said gas comprises only steam.

10. The process of claim 1, wherein said gas comprises steam and air.

11. The process of claim 1, wherein said at least one amide compound corresponds to the general formula (I):

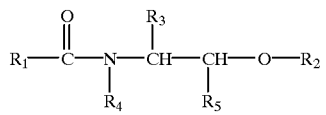

in which:
    $R_1$ is:
        a $C_9$–$C_{30}$, saturated or unsaturated, linear or branched hydrocarbon radical which is optionally substituted by one or more hydroxyl groups optionally esterified by a $C_{16}$–$C_{30}$ saturated or unsaturated fatty acid, or a radical R"—(NR—CO)$_n$—R' in which n is equal to 0 or 1, R is hydrogen or hydroxyethyl, and R' and R" are hydrocarbon radicals in which the sum of the carbon atoms is from 9 to 30, R' being a divalent radical,
    $R_2$ is a hydrogen atom or a (glycosyl)$_n$, (galactosyl)$_m$ or sulphogalactosyl radical, wherein n is an integer varying from 1 to 4 and m is an integer varying from 1 to 8,
    $R_3$ is a hydrogen atom, or a saturated or unsaturated $C_{16}$–$C_{27}$ hydrocarbon radical optionally substituted by one or more $C_1$–$C_{14}$ alkyl radicals, or a $C_{15}$–$C_{26}$ α-hydroxyalkyl radical, the hydroxyl group being optionally esterified by a $C_{16}$–$C_{30}$ α-hydroxy acid,
    $R_4$ is a hydrogen atom, a saturated or unsaturated $C_{16}$–$C_{27}$, hydrocarbon radical or a radical —CH$_2$—CHOH—CH$_2$—O—R$_6$ in which $R_6$ is a $C_{10}$–$C_{26}$ hydrocarbon radical,
    $R_5$ is a hydrogen atom or a mono- or polyhydroxylated $C_1$–$C_4$ hydrocarbon radical.

12. The process of claim 1, wherein said at least one amide compound is N-linoleoyldihydrosphingosine, N-oleoyldihydrosphingosine, N-palmitoyldihydrosphingosine, N-stearoyldihydrosphingosine, N-behenoyldihydrosphingosine, or a mixture of any of said compounds.

13. The process of claim 1, wherein said at least one amide compound is bis(N-hydroxyethyl-N-cetyl)malonamide, N-(2-hydroxyethyl)-N-(3-cetyloxy-2-hydroxypropyl)cetylamide or N-docosanoyl-N-methyl-D-glucamine.

14. The process of claim 1, wherein said at least one amide is present in a concentration ranging from 0.0001 to 30% by weight relative to the total weight of the composition.

15. The process of claim 14, wherein said at least one amide is present in a concentration ranging from 0.001 to 10% by weight.

16. A process for the treatment of human keratinous fibers comprising the steps of:
    (i) applying to human keratinous fibers a composition consisting essentially of at least one amide compound which has at least one fatty chain;

(ii) placing in contact with said human keratinous fibers a gas which contains steam and which is at a temperature of at least 75° C.;

(iii) cooling said fibers after said steam treatment; and wherein said human keratinous fibers are hair.

17. The process of claim 1, wherein said gas which contains steam comprises steam and at least one other gas, said at least one other gas being oxygen, nitrogen, air, or solvent vapour.

* * * * *